United States Patent
Bell et al.

(10) Patent No.: US 10,874,641 B2
(45) Date of Patent: Dec. 29, 2020

(54) METHODS OF TREATING ACUTE KIDNEY INJURY

(71) Applicant: Mitobridge, Inc., Cambridge, MA (US)

(72) Inventors: Eric Bell, Somerville, MA (US); Nan Ji, Arlington, MA (US); Dominique Stickens, Boston, MA (US); Taisuke Takahashi, Tsukuba (JP); Effie Tozzo, Lexington, MA (US)

(73) Assignee: Mitobridge, Inc., Cambridge, MA (US)

( * ) Notice: Subject to any disclaimer, the term of this patent is extended or adjusted under 35 U.S.C. 154(b) by 0 days.

(21) Appl. No.: 16/320,152

(22) PCT Filed: Jul. 27, 2017

(86) PCT No.: PCT/US2017/044118
§ 371 (c)(1),
(2) Date: Jan. 24, 2019

(87) PCT Pub. No.: WO2018/022851
PCT Pub. Date: Feb. 1, 2018

(65) Prior Publication Data
US 2019/0269655 A1  Sep. 5, 2019

Related U.S. Application Data

(60) Provisional application No. 62/367,758, filed on Jul. 28, 2016.

(51) Int. Cl.
| | | |
|---|---|---|
| *A61K 31/416* | (2006.01) | |
| *A61K 31/166* | (2006.01) | |
| *A61K 31/351* | (2006.01) | |
| *A61K 31/353* | (2006.01) | |
| *A61K 31/381* | (2006.01) | |
| *A61K 31/4184* | (2006.01) | |
| *A61P 13/12* | (2006.01) | |
| *A61K 33/243* | (2019.01) | |
| *A61K 9/00* | (2006.01) | |
| *A61K 31/454* | (2006.01) | |
| *A61K 31/502* | (2006.01) | |
| *A61K 31/5025* | (2006.01) | |
| *A61K 31/546* | (2006.01) | |
| *A61K 31/55* | (2006.01) | |
| *A61K 31/7048* | (2006.01) | |
| *A61K 38/13* | (2006.01) | |
| *A61K 31/5517* | (2006.01) | |
| *A61K 31/63* | (2006.01) | |
| *A61K 31/473* | (2006.01) | |
| *A61K 31/5377* | (2006.01) | |
| *A61K 31/519* | (2006.01) | |
| *A61K 31/496* | (2006.01) | |
| *A61K 45/06* | (2006.01) | |

(52) U.S. Cl.
CPC .......... *A61K 31/416* (2013.01); *A61K 9/0019* (2013.01); *A61K 31/166* (2013.01); *A61K 31/351* (2013.01); *A61K 31/353* (2013.01); *A61K 31/381* (2013.01); *A61K 31/4184* (2013.01); *A61K 31/454* (2013.01); *A61K 31/473* (2013.01); *A61K 31/496* (2013.01); *A61K 31/502* (2013.01); *A61K 31/5025* (2013.01); *A61K 31/519* (2013.01); *A61K 31/5377* (2013.01); *A61K 31/546* (2013.01); *A61K 31/55* (2013.01); *A61K 31/5517* (2013.01); *A61K 31/63* (2013.01); *A61K 31/7048* (2013.01); *A61K 33/243* (2019.01); *A61K 38/13* (2013.01); *A61P 13/12* (2018.01); *A61K 45/06* (2013.01)

(58) Field of Classification Search
None
See application file for complete search history.

(56) References Cited

PUBLICATIONS

Devalaraja-Narashimha et al., PARP-1 inhibits glycolysis in ischemic kidneys. J Am Soc Nephrol. Jan. 2009;20(1):95-103.
Kapoor et al., PARP inhibitor, olaparib ameliorates acute lung and kidney injury upon intratracheal administration of LPS in mice. Mol Cell Biochem. Feb. 2015;400(1-2):153-62.
Liu et al., Inhibition of Poly-(ADP-Ribose)Polymerase Protects the Kidney in a Canine Model of Endotoxic Shock. Nephron. 2015;130(4):281-92.
Yu et al., Inhibition of poly(ADP-ribose) polymerase attenuates acute kidney injury in sodium taurocholate-induced acute pancreatitis in rats. Pancreas. Nov. 2012;41(8):1299-1305.
International Search Report and Written Opinion for Application No. PCT/US2017/044118, dated Oct. 16, 2017, 12 pages.

*Primary Examiner* — Samantha L Shterengarts
(74) *Attorney, Agent, or Firm* — McCarter & English, LLP; Steven G. Davis; Wei Song (57) ABSTRACT

The present invention also contemplates a method of treating a human patient with acute kidney injury or reducing the likelihood of developing acute kidney injury in a human patient at risk of developing acute kidney injury comprising administering to the patient a poly-ADP ribose polymerase (PARP) inhibitor in a therapeutically effective dose so as to thereby treat the patient.

21 Claims, 3 Drawing Sheets

METHODS OF TREATING ACUTE KIDNEY INJURY

CROSS-REFERENCE TO RELATED APPLICATIONS

This application is a U.S. national stage filing, under 35 U.S.C. § 371(c), of International Application No. PCT/US2017/044118, filed on Jul. 27, 2017, which claims the benefit of priority to U.S. Provisional Patent Application No. 62/367,758, filed on Jul. 28, 2016. The entire contents of each of the aforementioned applications are incorporated herein by reference.

FIELD OF THE INVENTION

The present invention contemplates a method of treating a human patient with acute kidney injury or reducing the likelihood of developing acute kidney injury in a human patient at risk of developing acute kidney injury comprising administering to the patient a poly-ADP ribose polymerase (PARP) inhibitor in a therapeutically effective dose so as to thereby treat the patient.

BACKGROUND OF THE INVENTION

Acute kidney injury (AKI), previously known called acute renal failure (ARF), is a clinical syndrome characterized by rapid deterioration of renal function that occurs within days. The principal feature of AKI is an abrupt decline in glomerular filtration rate (GFR), resulting in the retention of nitrogenous wastes (urea, creatinine). In the general world population, 170-200 cases of severe AKI per million population occur annually. To date, there is no specific treatment for established AKI. Several drugs have been found to prophylactically ameliorate toxic and ischemic experimental AKI, as manifested by lower serum creatinine levels, reduced histological damage and faster recovery of renal function in different animal models. These include anti-oxidants, calcium channel blockers, diuretics, vasoactive substances, growth factors, anti-inflammatory agents and more. However, these drugs that have been studied in clinical trials showed no benefit, and their use in clinical AKI has not been approved. Treatment once AKI has developed is even more difficult.

Currently there are no satisfactory modes of therapy for the treating AKI in human patients with AKI or reducing the likelihood of developing AKI in a human patient at risk of developing acute kidney injury. Thus, there remains a need in the art to develop novel compounds for this purpose.

SUMMARY OF THE INVENTION

Figure 2:
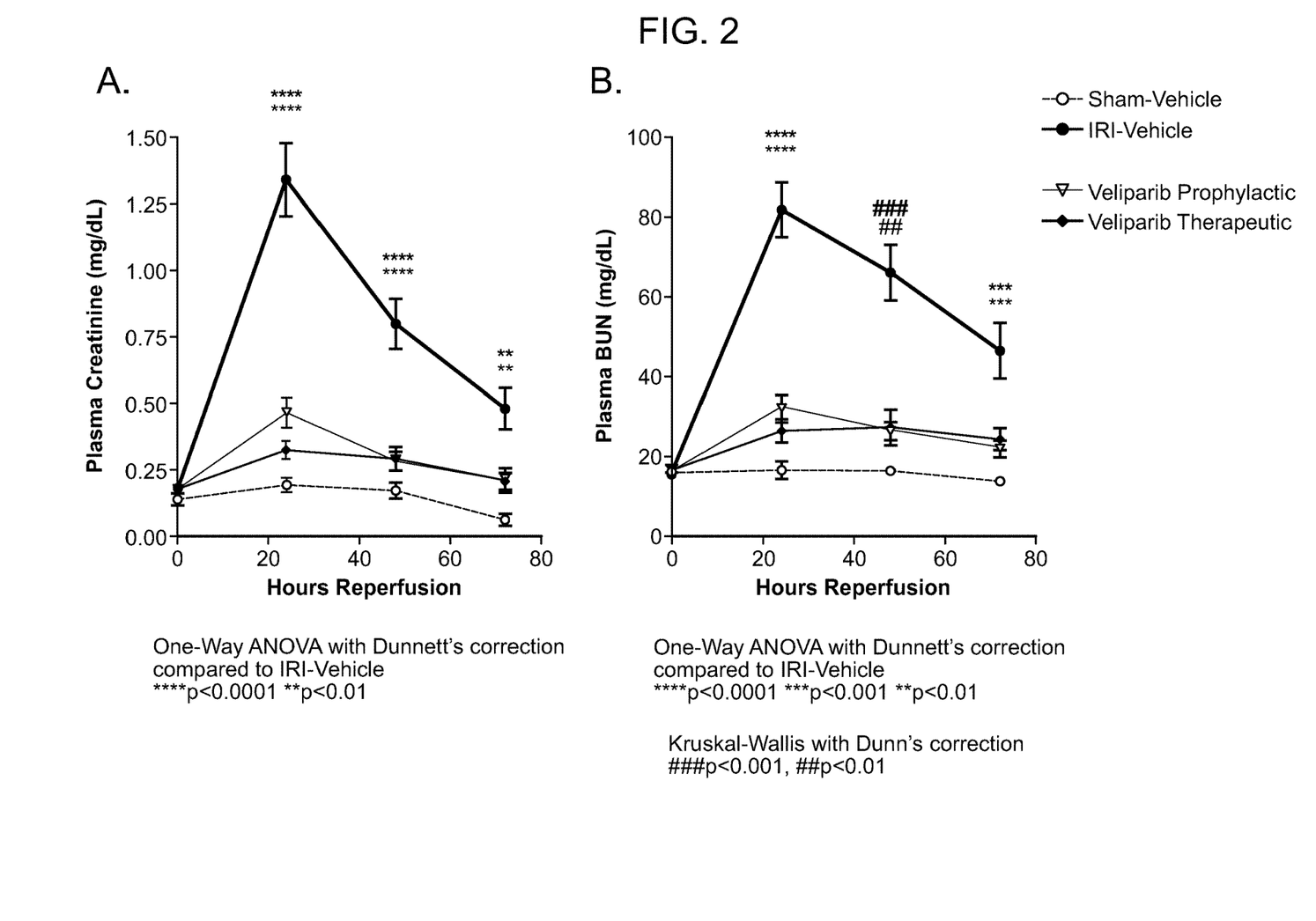
FIGS. 2A and 2B graphs showing veliparib attenuates induced increases in plasma creatinine levels and blood urea nitrogen (BUN) in rats after ischemic renal injury.
Figure 3:
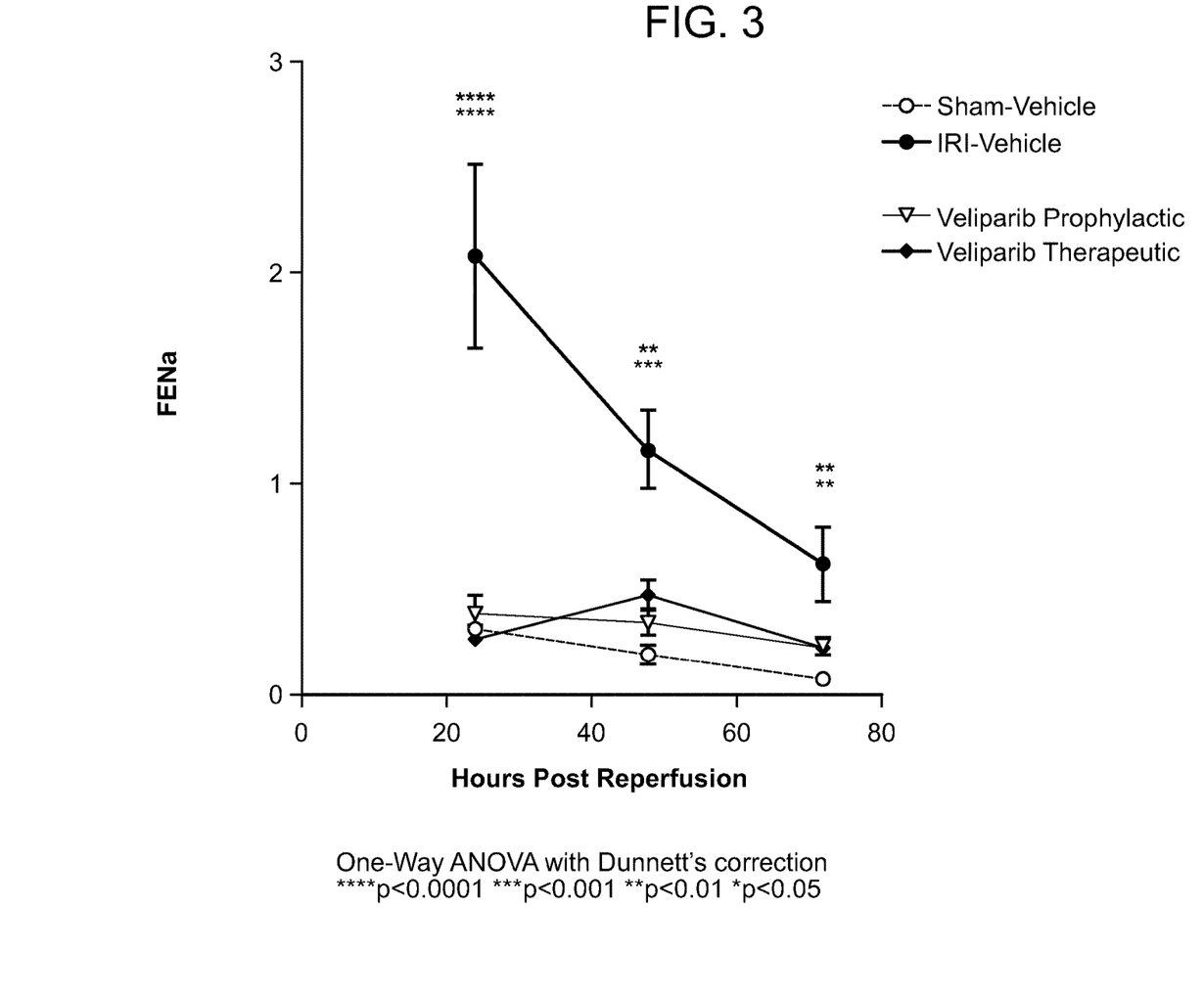
FIG. 3 is a graph showing veliparib improves fractional excretion of sodium (a measurement of tubular injury) after ischemic renal injury.

Provided herein, inter alia, are methods of using poly-ADP ribose polymerase (PARP) inhibitor for treating a human patient with acute kidney injury or reducing the likelihood of developing acute kidney injury in a human patient at risk of developing acute kidney injury. For example, FIGS. 2A, 2B, and 3, show attenuation of induced increases in plasma creatinine levels, blood urea nitrogen (BUN) and fractional excretion of sodium (a measurement of tubular injury) in rats after ischemic renal injury via administration of a PARP inhibitor (e.g., veliparib). Accordingly, specifically provided herein is a method of treating a human patient with acute kidney injury or reducing the likelihood of developing acute kidney injury in a human patient at risk of developing acute kidney injury, comprising administering to the subject a therapeutically effective amount of one or more PARP inhibitors.

Also provided herein is the use of one or more PARP inhibitors, or a pharmaceutical composition comprising one or more PARP inhibitors, for the preparation of a medicament for the treatment of a human patient with acute kidney injury or reducing the likelihood of developing acute kidney injury in a human patient at risk of developing acute kidney injury. Alternatively, a PARP inhibitor is used for the treatment of a human patient with acute kidney injury or reducing the likelihood of developing acute kidney injury in a human patient at risk of developing acute kidney injury.

In another embodiment, provided herein are PARP inhibitors, or a pharmaceutical composition comprising one or more PARP inhibitors, for use in a method for treating a human patient with acute kidney injury or reducing the likelihood of developing acute kidney injury in a human patient at risk of developing acute kidney injury.

DETAILED DESCRIPTION

PARP (poly-ADP ribose polymerase) participates in a variety of DNA-related functions including cell proliferation, differentiation, apoptosis, DNA repair and also has effects on telomere length and chromosome stability (d'Adda di Fagagna et al, 1999, Nature Gen., 23(1): 76-80).

Herein, the phrase "PARP inhibitor" refers to substances that selectively bind to the poly-ADP ribose polymerase enzyme and decrease its activity.

Substances can be tested for their PARP inhibitory activity using methods known in the art. See, for example, Cheung, et al. "A scintillation proximity assay for poly (ADP-ribose) polymerase," *Anal. Biochem.* 2000, Vol. 282, pp. 24-28.

PARP Inhibitors

Disclosed herein are methods of treating a human patient with acute kidney injury or reducing the likelihood of developing acute kidney injury in a human patient at risk of developing acute kidney injury with compounds that inhibit poly-ADP ribose polymerase (PARP).

A great preponderance of PARP inhibitors have been designed as analogs of benzamides, which bind competitively with the natural substrate $NAD^+$ in the catalytic site of PARP. The PARP inhibitors include, but are not limited to, benzamides, quinolones and isoquinolones, benzopyrones, methyl 3,5-diiodo-4-(4'-methoxy-3',5'-diiodo-phenoxy) benzoate (U.S. Pat. Nos. 5,464,871, 5,670,518, 5,922,775, 6,017,958, 5,736,576, and 5,484,951, each of which is incorporated herein by reference in its entirety). The PARP inhibitors include a variety of cyclic benzamide analogs (i.e. lactams) which are potent inhibitors at the $NAD^+$ site. Other PARP inhibitors include, but are not limited to, benzimidazoles and indoles (see, e.g., EP 841924, EP 127052, U.S. Pat. Nos. 6,100,283, 6,310,082, US 2002/156050, US 2005/054631, WO 05/012305, WO 99/11628, and US 2002/028815, each of which is incorporated herein by reference in its entirety).

PARP inhibitors may possess the following structural characteristics: 1) amide or lactam functionality; 2) an NH proton of this amide or lactam functionality could be conserved for effective bonding; 3) an amide group attached to an aromatic ring or a lactam group fused to an aromatic ring; 4) optimal cis-configuration of the amide in the aromatic plane; and 5) constraining mono-aryl carboxamide into heteropolycyclic lactams (Costantino et al., 2001, J Med Chem., 44:3786-3794); Virag et al., 2002, Pharmacol Rev., 54:375-29, the latter of which summarizes various PARP inhibitors, and each of which is incorporated herein by reference in its entirety. Some of the examples of PARP inhibitors include, but are not limited to, isoquinolinone and dihydrolisoquinolinone (for example, U.S. Pat. No. 6,664,269, and WO 99/11624, each of which is incorporated herein by reference in its entirety), nicotinamide, 3-aminobenzamide, monoaryl amides and bi-, tri-, or tetracyclic lactams, phenanthridinones (Perkins et al., 2001, Cancer Res., 61:4175-4183, incorporated herein by reference in its entirety), 3,4-dihydro-5-methyl-isoquinolin-1(2H)-one and benzoxazole-4-carboxamide (Griffin et al., 1995, Anticancer Drug Des, 10:507-514; Griffin et al., 1998, J Med Chem, 41:5247-5256; and Griffin et al., 1996, Pharm Sci, 2:43-48, each of which is incorporated herein by reference in its entirety), dihydroisoquinolin-1(2H)-nones, 1,6-naphthyridine-5(6H)-ones, quinazolin-4(3H)-ones, thieno[3,4-c]pyridin-4(5H)ones and thieno[3,4-d]pyrimidin-4(3H)-ones, 1,5-dihydroxyisoquinoline, and 2-methyl-quinazolin-4[3H]-one (Yoshida et al., 1991, J Antibiot (Tokyo,) 44: 111-112; Watson et al., 1998, Bioorg Med Chem., 6:721-734; and White et al., 2000, J Med Chem., 43:4084-4097, each of which is incorporated herein by reference in its entirety), 1,8-Napthalimide (Banasik et al., 1992, J Biol Chem, 267: 1569-1575; Watson et al., 1998, Bioo 2001, Nat Med., 7: 108-1 13; Li et al., 2001, Bioorg Med Chem Lett., 11:1687-1690 30:1071-1082, each of which is incorporated herein by reference in its entirety), tetracyclic lactams, 1,11b-dihydro-[1]benzopyrano-[4,3,2-de]isoquinolin-3[2H]-one, 1-methyl-4-phenyl-1,2,3,6-tetrahydropyridine (MPTP) (Zhang et al., 2000, Biochem Biophys Res Commun., 278:590-598; and Mazzon et al., 2001, Eur J Pharmacol, 415:85-94, each of which is incorporated herein by reference in its entirety). Other examples of PARP inhibitors include, but are not limited to, those detailed in the patents: U.S. Pat. Nos. 5,719,151, 5,756,510, 6,015,827, 6,100,283, 6,156,739, 6,310,082, 6,316,455, 6,121,278, 6,201,020, 6,235,748, 6,306,889, 6,346,536, 6,380,193, 6,387,902, 6,395,749, 6,426,415, 6,514,983, 6,723,733, 6,448,271, 6,495,541, 6,548,494, 6,500,823, 6,664,269, 6,677,333, 6,903,098, 6,924,284, 6,989,388, 6,277,990, 6,476,048, and 6,531,464, each of which is incorporated herein by reference in its entirety. Additional examples of PARP inhibitors include, but are not limited to, those detailed in the patent application publications: US 2004198693 A1, US 2004034078A1, US 2004248879A1, US 2004249841A 2005080096A1, US 2005171101A1, US 2005054631A1, WO 05054201A1, WO 05054209A1, WO 05054210A1, WO 05058843A1, WO 06003146A1, WO 06003147A1, WO 06003148A1, WO 06003150A1, and WO 05097750A1, each of which is incorporated herein by reference in its entirety.

In one embodiment, the PARP inhibitor is selected from the group consisting of:

(olaparib)

(talazoparib)

(niraparib)

(veliparib)

(rucaparib)

(E7449)

-continued (JPI-289)

(BGB-290)

(CEP-9722)

ABT767; and MP-124, or a pharmaceutically acceptable salt thereof.

In a specific embodiment, the PARP inhibitor is (veliparib)

or a pharmaceutically acceptable salt thereof.

In another specific embodiment, the inhibitor of poly-ADP ribose polymerase (PARP) is (olaparib)

or a pharmaceutically acceptable salt thereof.

In yet another specific embodiment, the inhibitor of poly-ADP ribose polymerase (PARP) is (talazoparib)

or a pharmaceutically acceptable salt thereof.

In still another specific embodiment, the inhibitor of poly-ADP ribose polymerase (PARP) is (niraparib)

or a pharmaceutically acceptable salt thereof.

In another specific embodiment, the inhibitor of poly ADP-ribose polymerase (PARP) is (rucaparib)

or a pharmaceutically acceptable salt thereof.

As used herein, the term "pharmaceutically-acceptable salt" refers to pharmaceutical salts that are, within the scope of sound medical judgment, suitable for use in contact with the tissues of humans and lower animals without undue toxicity, irritation, and allergic response, and are commensurate with a reasonable benefit/risk ratio. Pharmaceutically-acceptable salts are well known in the art. For example, S. M. Berge et al. describes pharmacologically acceptable salts in *J. Pharm. Sci.,* 1977, 66, 1-19.

Methods of Treatment

Provided herein are methods treating acute kidney injury in a human patient having or at risk of developing acute kidney injury.

Such methods comprise administering an effective amount of a PARP inhibitor to the human patient. In one embodiment, the PARP inhibitor is administered prior to the human patient developing acute kidney injury. Alternatively, the PARP inhibitor can be administered after the human patient develops acute kidney injury.

As used herein, the term "acute kidney injury" or "AKI", previously referred to as "acute renal failure" or "ARF", refers to an acute clinical syndrome characterized by rapid decline in renal functions, which is caused by a number of factors such as a reduction in renal blood flow, glomerulonephritis, use of nephrotoxic antibiotics and anticancer agents.

Acute kidney injury is defined as is defined by an abrupt decrease in kidney function, and can be diagnosed based on a patient exhibit changes in one or more of serum creatinine level, glomerular filtration rate, or urine output. For example, acute kidney injury can be characterized by a serum creatinine level of at least 1.5 times baseline, wherein baseline refers to the patient's serum creatinine level no more than 7 days prior. For example, a patient having acute kidney injury can have a serum creatinine level is 1.5 to 1.9 times baseline, 2.0 to 2.9 times baseline, or 3.0 or more times baseline. Alternatively, acute kidney injury can be characterized by an increase in serum creatinine of at least 0.3 mg/dL or at least 0.4 mg/dL.

Alternatively, acute kidney injury can be characterized by a glomerular filtration rate of less than 90 mL/min/1.73 m$^2$. For example, a patient having acute kidney injury can have glomerular filtration rate of 60-89 mL/min/1.73 m$^2$, 30-59 mL/min/1.73 m$^2$, 15-29 mL/min/1.73 m$^2$, or less than 15 mL/min/1.73 m$^2$.

Alternatively, acute kidney injury can be characterized by the patient having a urine output of less than 0.5 mL/Kg over 6 hours, less than 0.5 mL/Kg over 12 hours, less than 0.3 mL/Kg over 12 hours, or anuria for 12 or more hours.

Acute kidney injury can occur with specific kidney diseases (e.g., acute interstitial nephritis, acute glomerular and vasculitic renal diseases); non-specific conditions (e.g, ischemia, toxic injury); as well as extrarenal pathology (e.g., prerenal azotemia, and acute postrenal obstructive nephropathy). More than one of these conditions may coexist in the same patient and, more importantly, epidemiological evidence supports the notion that even mild, reversible AKI has important clinical consequences, including increased risk of death. Furthermore, because the manifestations and clinical consequences of AKI can be quite similar (even indistinguishable) regardless of whether the etiology is predominantly within the kidney or predominantly from outside stresses on the kidney, the syndrome of AKI encompasses both direct injury to the kidney as well as acute impairment of function.

In some embodiments, the patient being treated for AKI has diabetes, underlying renal insufficiency, nephritic syndrome, atherosclerotic disease, sepsis, hypotension, hypoxia, myoglobinuria-hematuria, or liver disease. In other embodiments, the patient is elderly, pregnant, a surgical patient, or has been exposed to a nephrotoxic agent.

In a specific embodiment, the patient being treated for AKI is a surgical patient. Accordingly, in certain embodiments, the compound is be administered to a surgical patient prior to and/or after surgery.

In another embodiment, the patient being treated for AKI has been exposed to a nephrotoxic agent is a drug or chemical capable of causing AKI. Drugs or chemicals capable of causing acute kidney injury include, but are not limited to, cisplatin; gentamicin; cephaloridine; cyclosporine; amphotericin; carbon tetrachloride; trichloroethylene; and dichloroacetylene.

As such, a patient with any of the conditions mentioned in the previous three paragraphs is at risk for developing AKI and can be treated with a PARP inhibitor in accordance with the disclosed methods to reduce the likelihood of developing AKI.

Pharmaceutical Compositions and Administration Thereof

A. Additional Therapeutic Agents

Pharmaceutical compositions are disclosed that include one or more PARP inhibitor and typically at least one additional substance, such as an excipient, a known therapeutic other than those of the present disclosure, and combinations thereof. In some embodiments, a PARP inhibitor can be used in combination with other agents known to have beneficial, additive or synergistic activity with the PARP inhibitor.

B. Excipients and Dosage Forms

"Pharmaceutically acceptable excipient" and "pharmaceutically acceptable carrier" refer to a substance that aids the formulation and/or administration of an active agent to and/or absorption by a subject and can be included in the compositions of the present disclosure without causing a significant adverse toxicological effect on the subject. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical excipients are suitable for use with disclosed compounds.

The particular mode of administration and the dosage regimen will be selected by the attending clinician, taking into account the particulars of the case (e.g. the subject, the disease, the disease state involved, the particular treatment, and whether the treatment is prophylactic). Treatment can involve daily or multi-daily or less than daily (such as weekly or monthly etc.) doses over a period of a few days to months, or even years. However, a person of ordinary skill in the art would immediately recognize appropriate and/or equivalent doses looking at dosages of approved compositions for treating a mitochondrial disease using the disclosed PPARα agonists for guidance.

C. Methods of Administration

The precise amount of compound administered to provide a "therapeutically effective amount" to the subject will depend on the mode of administration, the type, and severity of the cancer, and on the characteristics of the subject, such as general health, age, sex, body weight, and tolerance to drugs. The skilled artisan will be able to determine appropriate dosages depending on these and other factors. When administered in combination with other therapeutic agents, e.g., when administered in combination with an anti-cancer agent, an "effective amount" of any additional therapeutic agent(s) will depend on the type of drug used. Suitable dosages are known for approved therapeutic agents and can be adjusted by the skilled artisan according to the condition of the subject, the type of condition(s) being treated and the amount of a compound of the invention being used by following, for example, dosages reported in the literature and recommended in the *Physician's Desk Reference* (57th ed., 2003).

The term "therapeutically effective amount" means an amount when administered to the subject which results in beneficial or desired results, including clinical results, e.g., inhibits, suppresses or reduces the symptoms of the condition being treated in the subject as compared to a control. For example, a therapeutically effective amount can be given in unit dosage form (e.g., 0.1 mg to about 50 g per day, alternatively from 1 mg to about 5 grams per day; and in another alternatively from 10 mg to 1 gram per day).

The terms "administer", "administering", "administration", and the like, as used herein, refer to methods that may be used to enable delivery of compositions to the desired site of biological action. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, *The Pharmacological Basis of Therapeutics*, current ed.; Pergamon; and Remington's, *Pharmaceutical Sciences* (current edition), Mack Publishing Co., Easton, Pa.

As used herein, the terms "co-administration", "administered in combination with", and their grammatical equivalents, are meant to encompass administration of two or more therapeutic agents to a single subject, and are intended to include treatment regimens in which the agents are administered by the same or different route of administration or at the same or different times. In some embodiments the one or more compounds described herein will be co-administered with other agents. These terms encompass administration of two or more agents to the subject so that both agents and/or their metabolites are present in the subject at the same time. They include simultaneous administration in separate compositions, administration at different times in separate compositions, and/or administration in a composition in which both agents are present. Thus, in some embodiments, the compounds described herein and the other agent(s) are administered in a single composition. In some embodiments, the compounds described herein and the other agent(s) are admixed in the composition.

The particular mode of administration and the dosage regimen will be selected by the attending clinician, taking into account the particulars of the case (e.g. the subject, the disease, the disease state involved, the particular treatment, and whether the treatment is prophylactic). Treatment can involve daily or multi-daily doses over a period of a few days. However, a person of ordinary skill in the art would immediately recognize appropriate and/or equivalent doses looking at dosages of approved compositions for treating a mitochondria-related disease using the disclosed compounds for guidance.

Pharmaceutical compositions are disclosed that include a PARP inhibitor, and typically at least one additional substance, such as an excipient, a known therapeutic other than those of the present disclosure, and combinations thereof.

The pharmaceutical composition of the invention is formulated to be compatible with its intended route of administration. In an embodiment, the composition is formulated in accordance with routine procedures as a pharmaceutical composition adapted for intravenous, subcutaneous, intramuscular, oral, intranasal, or topical administration to human beings. In preferred embodiments, the pharmaceutical composition is formulated for intravenous administration.

EXEMPLIFICATION

Example

Acute kidney injury (AKI) is a clinical condition characterized by a rapid decline in kidney function and is often associated with high morbidity and mortality. The precise etiology of ischemia/reperfusion (I/R)-induced AKI is yet not fully understood and is thought to involve multiple factors. The prevention of acute kidney injury and its progression represents a great challenge particularly in renal transplanted patients. Therefore, animal models of renal ischemia/reperfusion (I/R) are important to understand pathophysiology and potential treatment strategies for AKI. The present study evaluated the efficacy of a test compound, namely veliparib (shown below), (veliparib)

in a rat model of ischemia/reperfusion induced kidney injury.

1. Study Details

Test System:
  Species: *Rattus norvegicus*
  Strain: Sprague Dawley
  Sex/age: Male, 8-9 weeks
  Body weight: 180-200 g
  Number of animals: 46

2. Animal Care and Housing

Animal experiments were conducted in accordance with the guidelines of the Committee for the Purpose of Control and Supervision of Experiments on Animals (CPCSEA), Government of India the Association for Assessment and Accreditation of Laboratory Animal Care international (AAALAC). The 'Form B' for carrying out animal experimentation were reviewed and approved by the Institutional Animal Ethics Committee. PPE (personal protective equipment) will be used appropriately to carry out the experiment (safety glasses, gloves, lab coats and mask). Animals were maintained in a controlled environment with 22±3° C. temperature, 50±20% humidity, a light/dark cycle of 12 hours each and 15-20 fresh air changes per hour. Animals were housed in metabolic cages 2 days prior (acclimatization) until day 3 post surgery. Animals were maintained on rodent chow diet ad libitum and were given free access to fresh autoclaved potable drinking water.

3. Experimental Plan i. All animals were numbered and kept in acclimatization for a period of 5-7 days, with 2 days acclimatization on metabolic cages before, initiation of the experiment.

ii. Animals were randomized into different treatment groups based on their body weight and assigned a permanent number.

iii. Body weight measurements were made once at randomization, also daily just prior to compound dosing and prior to termination. All body weights were recorded.

iv. Treatment with test compound(s) varied based on dose group (see table) that follows different dosing paradigms. The time of each dose administration was recorded.

1. The dosing schedule for groups 1 and 2 was as follows: a 5 mL/kg BID dose with vehicle starting Day −1 through Day 2 with the final dose on Day 3 occurring 2 hours prior to takedown.

2. The dosing schedule for group 3 with veliparib was 25 mg/kg BID starting on Day −1. The Day 0 (day of surgery) morning dose was administered 1 hour prior to surgery and then the $2^{nd}$ dose before the dark cycle. BID dosing continued on Day 1 and Day 2 with the last dose occurring 2 hours before takedown on Day 3.

3. The dosing schedule for group 4 with veliparib was 25 mg/kg starting 4 hours after surgery on Day 0 (day of surgery) and this served as the only dose for the day. BID dosing continued on Days 1 and 2 with the last dose 2 hours before takedown on Day 3.

v. Surgical Procedure: Surgeries for this study occurred within 2 hours of each other to accommodate dosing just before surgery and just prior to the start of the dark cycle. Additionally, all dosing, fluid collections and sacrifice occurred at similar time points among the groups. Rats were anesthetized with isoflurane and placed on heated surgical platform (temperature controlled heating pads) on its ventral surface. A skin incision was made on the dorsal surface and both kidneys will be exposed through flank incisions and the fat was cleared gently to isolate the renal pedicles. Vascular clips then were applied to the renal pedicels and occluded for 45 minutes. Kidneys were placed in the abdominal cavity to maintain temperature and the incision was covered with sterile gauze soaked with 0.9% saline. After 45 min, the clips were removed, reperfusion was monitored (change in kidney color) for 1-2 min and the surgical sites were sutured. Animals that did not properly re-perfuse were not included in the remaining of the study. 1 mL of physiological saline was administered intraperitoneally after closing the wound to prevent dehydration. A suitable analgesic (meloxicam) was administered post operatively to all animals. The sham-operated group was subjected to similar surgical procedures, except that the occluding clamp was not applied.

vi. Postsurgical care and recovery: Animals were monitored until recovery from anesthesia and returned to their metabolic cage. Thereafter, animals were observed every day for general clinical signs and symptoms and mortality.

vii. Urine Parameters: Rats were individually housed in metabolic cages throughout the study and urine was collected at 6, 24, 48 and 72 hours post ischemia. For the 6 hour collection, urine volume was measured and recorded (to the nearest 1.0 mL) and samples were clarified by centrifugation (3000 rpm for 10 minutes). After centrifugation an appropriate sized aliquot was collected for Kim-1 and urinary creatinine levels. In addition, a 300 µL aliquot was retained and frozen for additional urinary biomarkers. Any remaining urine from this collection was added back to the 24-hour urine collection sample. For all other remaining urine collections, the total volume of urine was measured and recorded (to the nearest 1.0 mL) and centrifuged at approximately 3000 rpm for 10 minutes at 5° C.±3° C. A single aliquot from the supernatant was collected into an individually labeled polypropylene tube. Urine samples were maintained in wet ice and analyzed on the same day of collection or maintained frozen until urea, creatinine, sodium and Kim-1 were measured. Any remaining urine was discarded; the urine sediment was retained and frozen at approximately −70° C.

viii. Plasma Parameters: After 24, 48 and 72 hours of reperfusion, blood was collected by retro orbital puncture under mild isoflurane anesthesia. Blood samples were transferred into appropriately-sized purple top ($K_3$-EDTA) collection tubes. Samples were centrifuged at approximately 3000 rpm for 10 minutes at 5° C.±3° C. All plasma samples were transferred into individually labeled tubes analyzed for blood urea nitrogen levels (BUN), creatinine, sodium and cystatin C. Remaining plasma samples (at least 100 µL) were immediately placed on dry ice.

ix. Tissue parameters: After 72 hours of reperfusion, animals were subjected to isoflurane anesthesia and after blood was collected by cardiac puncture the right kidney was quickly collected, the cortex was rapidly dissected out (remove medullary portion) and then freeze-clamped with instruments cooled to liquid nitrogen temperatures (this was used for measuring extremely liable metabolites). The left kidney was harvested and cut sagittally with one half-fixed in 10% neutral buffered formalin. The cortex of the other half kidney was dissected out (remove medullary portion) and split into two tubes, one 1.5 mL Eppendorf tube (this sample was for PK analysis—sample not to exceed 100 mg), the remaining kidney cortex was placed in a 2 mL tube, flash frozen in liquid nitrogen, stored at −80° C. until analyzed for biochemical analysis of glutathione peroxidase (GSH) and superoxide dismutase (SOD) activity.

4. Experimental Groups i. Groups and Treatment Schedule:

TABLE 1

Groups and treatment schedule

| Group No. | N | Surgery | Treatment | Schedule Day-1 | Day 0 (Day of Surgery) Before Surgery | Day 0 (Day of Surgery) After Surgery |
|---|---|---|---|---|---|---|
| 1 | 4 | Sham | Vehicle[a] | BID, second dose before start of dark cycle | Immediately before animals are anesthetized for surgery | Just before the start of the dark cycle |
| 2 | 8 | IRI | Vehicle[a] | BID, second dose before start of dark cycle | Immediately before animals are anesthetized for surgery | Just before the start of the dark cycle |
| 3 | 8 | IRI | Veliparib | BID, second dose before start of dark cycle | morning dose (1 hour before surgery) | Just before the start of the dark cycle |
| 4 | 8 | IRI | Veliparib | none | none | 4 hours after reperfusion |

| Group No. | Schedule Days 1 (24 hr) and 2 (48 hr) | Day 3 (72 hr) | TDD (mg/kg) | BID (mg/kg) | Conc. (mg/mL) | Dose volume (mL/kg) | ROA | Frequency |
|---|---|---|---|---|---|---|---|---|
| 1 | BID, second dose before start of dark cycle | dose 2 hr before sacrafice | NA | NA | NA | 5 | PO | BID[b] |
| 2 | BID, second dose before start of dark cycle | dose 2 hr before sacrafice | NA | NA | NA | 5 | PO | BID[b] |
| 3 | BID, second dose before start of dark cycle | dose 2 hr before sacrafice | 50 | 25 | 5 | 5 | PO | BID[b] |
| 4 | BID, second dose before start of dark cycle | dose 2 hr before sacrafice | 50 | 25 | 5 | 5 | PO | BID[b] |

[a]The vehicle will be 0.9% Saline pH 4
[b]The last dose will be administered 2 hours prior to sacrifice ii. Formulations a. Vehicle: 0.9% saline adjusted to pH 4.0 with HCl.

b. Veliparib: Formulation was prepared fresh daily by dissolving veliparib in 0.9% saline and adjusting the pH to 4.0 with HCl.

4. Study Design

Figure 1:
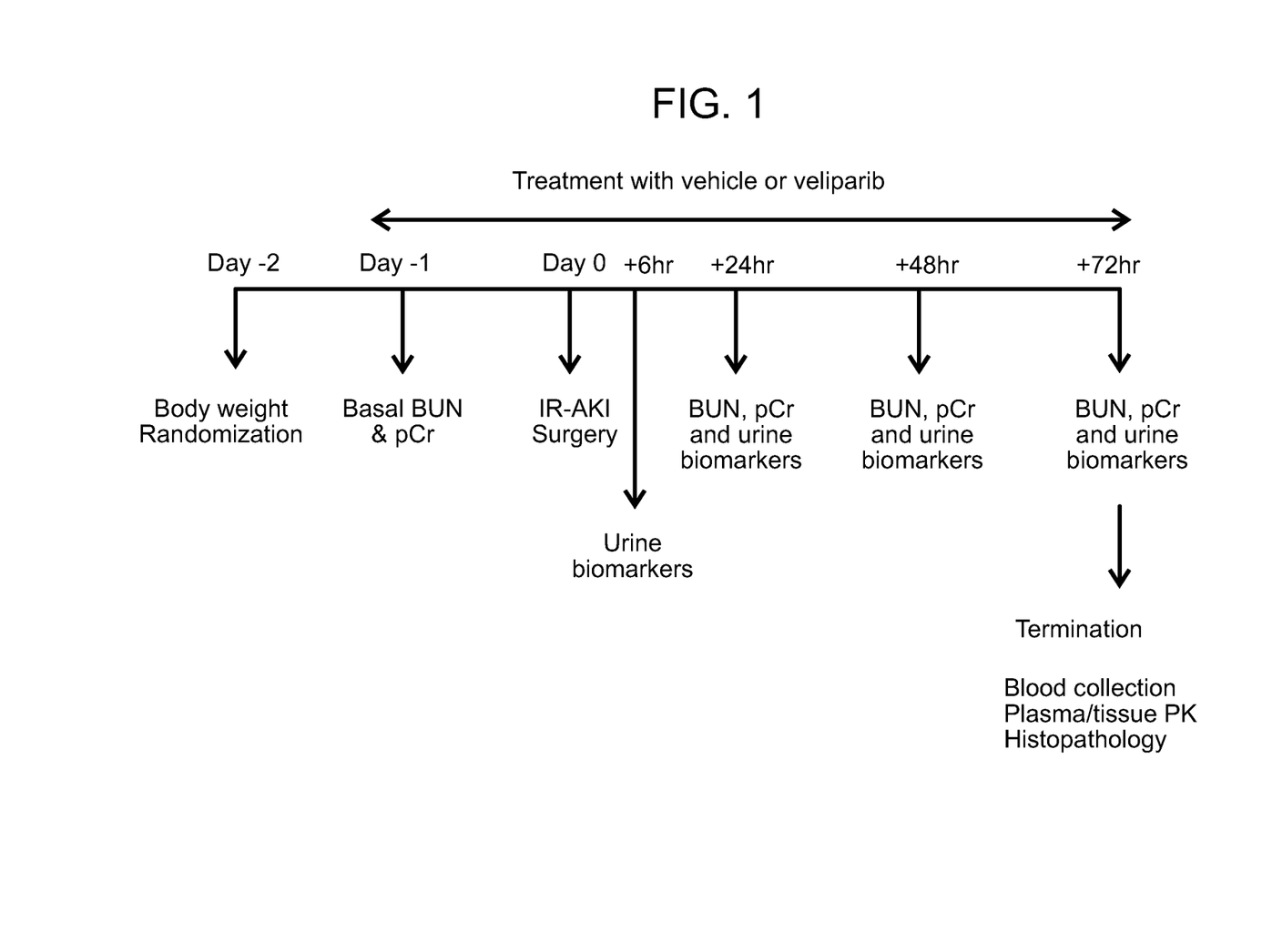
FIG. 1 is a diagram showing the design of the study described in the Exemplification.

The study design is shown in FIG. 1.

5. Termination 72 hours after reperfusion, animals were subjected to isoflurane anesthesia and 500 μL of blood (target) were collected by cardiac puncture after opening the thoracic cavity, for plasma separation. Samples were centrifuged and plasma was separated into fresh tubes and stored at −80° C. until analysis. Organs and tissues were collected as mentioned above.

6. Parameters
   a. General Health and clinical signs: Animals were observed every day
   b. Body weight: Once at randomization, daily during dosing and prior to termination.
   c. Bilateral ischemic AKI: On Day 0
   d. Plasma Parameters: BUN and Creatinine Day −1 (basal levels); BUN, Creatinine, Cystatin C, Sodium at 24, 48 and 72 h after renal ischemia.
   e. Urine parameters: Creatinine in urine at 6 hrs and Urea, creatinine, Sodium in urine at 6, 24, 48 and 72 h after renal ischemia
      Kim-1, MCP-1, Ngal (Lipocalin), FABP1 & TIMP1 depending on outcome of primary endpoints
   f. Termination and organ collection: 72 hours after renal ischemia, blood was collected and animals were euthanized. Organs were collected and stored under appropriate conditions.
   g. Kidney tissue parameters:
      GSH, and SOD levels were estimated in kidney homogenates
   h. Histopathology and scoring (qualitative assessment) in kidney:
      Hematoxylin and eosin (H & E) and Periodic-acid Schiff (PAS) staining and histopathological analysis of tubular cell necrosis, tubular dilation, tubular casts, inflammatory cell infiltration, loss of brush borders, and tubular regeneration.
   i. Plasma & Tissue PK: Tissue/plasma PK for veliparib.

7. Conclusion

The results of this study showed that veliparib attenuates induced increases in plasma creatinine levels, blood urea nitrogen (BUN) and fractional excretion of sodium (a measurement of tubular injury) in rats after ischemic renal injury (FIGS. 2A, 2B, and 3).

BIBLIOGRAPHY

1. Basile D P, Donohoe D, Cao X, Van Why S K. Resistance to ischemic acute renal failure in the Brown Norway rat: a new model to study cytoprotection. Kidney international. 2004 Jun. 1; 65(6):2201-11.
2. Peng H, Mao Y, Fu X, Feng Z, Xu J. Comparison of biomarkers in rat renal ischemia-reperfusion injury. International journal of clinical and experimental medicine. 2015; 8(5):7577.
3. Benjamin D. Humphreys, * Vincenzo Cantaluppi, † Didier Portilla, ‡ Kai Singbartl, § Li Yang, | Mitchell H. Rosner, ‡ John A. Kellum, § and Claudio Ronco, ¶ for the Acute Dialysis Quality Initiative (ADQI) XIII Work Group. Targeting Endogenous Repair Pathways after A M. J Am Soc Nephrol 2016; 27: 990-998.
4. David P. Basile, Joseph V. Bonventre, Ravindra Mehta, Masaomi Nangaku, Robert Unwin, Mitchell H. Rosner, John A. Kellum, and Claudio Ronco, the ADQI XIII Work Group. Progression after AKI: Understanding Maladaptive Repair Processes to Predict and Identify Therapeutic Treatments. J Am Soc Nephrol 2016; 27: 687-697.
5. Monica Parks and Kathleen D. Liu. Clinical trials in AKI: is the end in sight? Nature Reviews/Nephrology 2016 (May) 12: 263-264.

What is claimed is:

1. A method of treating a human patient for acute kidney injury comprising administering an effective amount of a poly-ADP ribose polymerase (PARP) inhibitor to the human patient, wherein the patient is elderly, pregnant, a surgical patient, or has been exposed to a nephrotoxic agent, wherein the nephrotoxic agent is a drug or chemical capable of causing acute kidney injury.

2. The method of claim 1, wherein the poly-ADP ribose polymerase (PARP) inhibitor is administered after developing acute kidney injury.

3. The method of claim 2, wherein the acute kidney injury is characterized by a serum creatinine level of at least 1.5 times baseline, wherein baseline refers to the patient's serum creatinine level no more than 7 days prior.

4. The method of claim 3, wherein the serum creatinine level is 1.5 to 1.9 times baseline, and the acute kidney injury is characterized by an increase in serum creatinine of at least 0.3 mg/dL.

5. The method of claim 3, wherein the serum creatinin level is 3.0 or more times baseline.

6. The method of claim 2, wherein the acute kidney injury is characterized by an increase in serum creatinine of at least 0.3 mg/dL.

7. The method of claim 6, wherein the acute kidney injury is characterized by an increase in serum creatinine of at least 0.4 mg/dL, wherein the acute kidney injury is characterized by a glomerular filtration rate of 60-89 mL/min/1.73 m$^2$.

8. The method of claim 2, wherein the acute kidney injury is characterized by a glomerular filtration rate of less than 90 mL/min/1.73 m$^2$.

9. The method of claim 8, wherein the glomerular filtration rate is 60-89 mL/min/1.73 m$^2$, wherein the acute kidney injury is characterized by the patient having a urine output of less than 0.5 mL/Kg over 6 hours.

10. The method of claim 8, wherein the glomerular filtration rate is less than 15 mL/min/1.73 m$^2$.

11. The method of claim 2, wherein the acute kidney injury is characterized by the patient having a urine output of less than 0.5 mL/Kg over 6 hours.

12. The method of claim 11, wherein the urine output is less than 0.3 mL/Kg over 12 hours.

13. The method of claim 2, wherein the acute kidney injury is characterized by the patient having anuria for 12 or more hours.

14. The method of claim 1, wherein the poly-ADP ribose polymerase (PARP) inhibitor is selected from the group consisting of:

(olaparib)

(talazoparib)

(niraparib)

(veliparib)

(rucaparib)

(E7449)

(JPI-289)

(BGB-290)

(CEP-9722)

ABT767; and MP-124, or a pharmaceutically acceptable salt thereof.

15. The method of claim 1, wherein the patient is suffering from acute interstitial nephritis, acute glomerular renal disease, acute vasculitic renal disease, ischemia, toxic injury, prerenal axotemia, or acute postrenal destructive nephropathy.

16. The method of claim 1, wherein the patient has diabetes, underlying renal insufficiency, nephritic syndrome, atherosclerotic disease, sepsis, hypotension, hypoxia, myoglobinuria-hematuria, or liver disease.

17. The method of claim 1, wherein the nephrotoxic agent is a drug or chemical capable of causing acute kidney injury, wherein the drug or chemical is one or more of the compounds selected from the group consisting of: cisplatin; gentamicin; cephaloridine; cyclosporine; amphotericin; carbon tetrachloride; trichloroethylene; and dichloroacetylene.

18. The method of claim 1, wherein the human patient is a surgical patient.

19. The method of claim 18, wherein the poly-ADP ribose polymerase (PARP) inhibitor is administered to the surgical patient prior to surgery.

20. The method of claim 18, wherein the poly-ADP ribose polymerase (PARP) inhibitor is administered to the surgical patient after surgery.

21. The method of claim 18, wherein the poly-ADP ribose polymerase (PARP) inhibitor is selected from the group consisting of:

(olaparib)

(talazoparib)

-continued (niraparib)

(veliparib)

(rucaparib)

(E7449)

(JPI-289)

(BGB-290)

(CEP-9722)

ABT767; and MP-124, or a pharmaceutically acceptable salt thereof.